US006630502B2

(12) United States Patent
Bergey et al.

(10) Patent No.: US 6,630,502 B2
(45) Date of Patent: *Oct. 7, 2003

(54) METHOD FOR PREVENTING, STABILIZING OR CAUSING REGRESSION OF ATHEROSCLEROSIS EMPLOYING A COMBINATION OF A CHOLESTEROL LOWERING DRUG AND AN ACE INHIBITOR

(75) Inventors: James L. Bergey, Lansdale, PA (US); Werner Tschollar, Lawrenceville, NJ (US); Cary S. Yonce, Newtown; James C. Kawano, Narberth, both of PA (US)

(73) Assignee: E.R. Squibb & Sons, Inc., Princeton, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 07/801,207

(22) Filed: Dec. 2, 1991

(65) Prior Publication Data

US 2003/0149101 A1 Aug. 7, 2003

Related U.S. Application Data

(63) Continuation-in-part of application No. 07/524,266, filed on May 15, 1990, now abandoned.

(51) Int. Cl.[7] .................. A61K 31/40; A61K 31/35; A61K 31/21
(52) U.S. Cl. .................. 514/423; 514/460; 514/510; 514/824; 514/424
(58) Field of Search .................. 514/423, 460, 514/510, 824, 424

(56) References Cited

U.S. PATENT DOCUMENTS

| | | | |
|---|---|---|---|
| 4,105,776 A | 8/1978 | Ondetti et al. .............. | 424/274 |
| 4,319,039 A | 3/1982 | Albers-Schonberg ....... | 560/256 |
| 4,346,227 A | 8/1982 | Terahara .................... | 560/119 |
| 4,668,699 A | 5/1987 | Hoffman et al. ............ | 514/460 |
| 4,871,721 A | 10/1989 | Biller ......................... | 514/102 |
| 4,924,024 A | 5/1990 | Biller ......................... | 558/202 |
| 5,061,694 A | * 10/1991 | Aberg et al. ................ | 514/19 |

OTHER PUBLICATIONS

Weinstein and Heider, "Protective action of calcium channel antagonists in atherogenesis and vascular injury," Am. J. Hypertens. 2:205–12, 1989.
Goldschmidt and Tallarida, "Effect of captopril exposure on endothelium–dependent relaxation in rabbit aorta," F.A.S.E.B. Journal 3:A1195, 1989.
Costa et al, "Use of captopril to reduce serum lipids in hypertensive patients with hyperlipidemia," Am. J. Hyperten. 1:2219–2239, 1988.
Edelman et al, "Hyperkalemia During Treatment with HMG CoA Reductase Inhibitor," N. Engl. J. Med. (320, No. 18, 1219–20, 1989).
Zorn et al, "Prevention of Arteriosclerotic Lesions with Calcium Antagonists or Captopril in Dirrerent Rat Hypertension Models," J. Cardiovasc. Pharmacol. vol. 12 (Suppl. 6), 1988.
Someya et al, "Suppressive Effect of Captopril on Platelet Aggregation in Essential Hypertension," J. Cardiovasc. Pharmacol. 6:840–843, 1984.
Mizuno et al, "The effects of the antiotensin I–converting enzyme inhibitor, captopril, on serum lipoperoxides level and the renin–angiotensin–aldosterone and kallikrenin–kinin system in hypertensive patients," Nippon Naibunpi Gakkai Zasshi Feb. 20, 1984.
Mizuno et al, "Acute effects of captopril on serum lipid peroxides level in hypertensive patients," Tohoku J. Exp. Med., May, 1984, 143(1) p. 127–8.
Overturf et al, "Hypertension and Atherosclerosis in Cholesterol–Fed Rabbits Part 1. MIld, Two–Kidney, One–Clip Goldblatt Hypertension treated with Enalapril," Atherosclerosis, 59:283–299, 1986.
Cecil, Textbook of Medicine, 16 Ed., pp 239 to 241.
McClard et al, "Novel Phosphonylphosphinyl (P–C–P–C–) Analogues of Biochemically Interesting Diphosphates. Syntheses and Properties of P–C–P–C– Analogues of Isopentenyl Diphosphate and Dimethylallyl Diphosphate," J.A.C.S. 1987, 190, 5544–5545.
Biller et al., "Isoprenoid (Phosphinylmethyl) phosphonates as Inhibitors of Squalene Synthetase," Journal of Medicinal Chemistry, 1988, vol. 31, No. 10, pp 1869–1871.
Watanbe et a. "Prevention effect of pravastatin soduim a potent inhibitor of 3 hyrdroxy–3–methylglutaryl coezyme A reductase on coronary atherosclerosis and xanthoma i WHHL rabbits." 1988 960(3), 294–302 ISSN: 0006–3002.*
Watanabe et al., Biochimica et Biophysica Acts, 960 (1988) pp. 294–302.
Kowala et al., Journal of Cardiovascular Pharmacology, 1998, vol. 32, No. 1, pp. 29–38.

* cited by examiner

Primary Examiner—Theodore J. Criares
Assistant Examiner—Jennifer Kim
(74) Attorney, Agent, or Firm—Burton Rodney; Sammy G. Duncan, Jr.

(57) ABSTRACT

A method is provided for slowing the progression of atherosclerosis in hypertensive or normotensive patients and reducing or eliminating atherosclerotic lesions in such patients by administering a combination of a cholesterol lowering drug such as pravastatin, and an ACE inhibitor, especially one containing a mercapto moiety, such as captopril or zofenopril.

9 Claims, No Drawings

US 6,630,502 B2

METHOD FOR PREVENTING, STABILIZING OR CAUSING REGRESSION OF ATHEROSCLEROSIS EMPLOYING A COMBINATION OF A CHOLESTEROL LOWERING DRUG AND AN ACE INHIBITOR

REFERENCE TO OTHER APPLICATIONS

This application is a continuation-in-part of application Ser. No. 07/524,266, filed May 15, 1990, now abandoned.

FIELD OF THE INVENTION

The present invention relates to a method for preventing, stabilizing or causing regression of atherosclerosis in mammalian species by administering a combination of a cholesterol lowering drug, such as an HMG CoA reductase inhibitor, for example, pravastatin, and an ACE inhibitor, preferably an ACE inhibitor containing a mercapto moiety, such as captopril or zofenopril, and to a pharmaceutical combination for use in such method.

BACKGROUND OF THE INVENTION

The proatherosclerotic effect of elevated serum cholesterol on vascular tissue is well documented (Weinstein and Heider, "Protective action of calcium channel antagonists in atherogenesis and vascular injury," Am. J. Hypertens. 2: 205–12,1989).

It is also well known that platelets which may participate in the atherogenic process do so via mediators released upon activation (thromboxane $A_2$ (TXA$_2$), platelet aggregating factor (PAF), etc.,) which in turn stimulate smooth muscle cells to contract as well as to proliferate. The latter effect is an important step in atherosclerotic plaque formation (Hoak, "Platelets and atherosclerosis," Semin. Thromb. Hemost. 14: 202–5, 1988). Many of the stimulatory effects of prostanoids on vascular smooth muscle can be reversed by endothelium derived relaxing factor (EDRF), a substance whose metabolic stability and/or efficacy appears to be enhanced by captopril (Goldschmidt and Tallarida, "Effect of captopril exposure on endothelium-dependent relaxation in rabbit aorta," F.A.S.E.B. Journal 3: A1195, 1989).

In addition, it has recently been found that captopril significantly reduced serum cholesterol (−18%) and increased HDL (27%) in hypercholeserolemic patients (Costa et al, "Use of captopril to reduce serum lipids in hypertensive patients with hyperlipidemia," Am. J. Hyperten. 1: 2219–2239, 1988). There is no evidence that these therapeutic effects result from inhibition of the cholesterol synthetic pathway. Thus, the therapeutic mechanism for ACE inhibitors is different from that of HMG CoA reductase inhibitors such as pravastatin and lovastatin.

Edelman, S. et al, N. Engl. J. Med. (320, No. 18, 1219–20, 1989), "Hyperkalemia During Treatment with HMG CoA Reductase Inhibitor," discloses a case where a patient received lovastatin (1s) for hyperlipidemia and whose hypertension was initially well controlled with lisinopril. "LS treatment was started when cholestyramine and niacin treatment was not successful. The patient developed myositis and hyperkalemia and recovered after emergency treatment and withdrawal of LS. He later resumed taking LS (without consultation) and again developed severe myositis and hyperkalemia. He recovered when LS was withdrawn. Care is cautioned when LS and lisinopril are given in combination to patients atrisk of hyperkalemia."

European Patent Application 0219782 to Scholkens (Hoechst) discloses the treatment of atherosclerosis, thrombosis and/or peripheral vascular disease in mammals using an angiotensin converting enzyme (ACE) inhibitor or its physiologically tolerable salts. It further discloses that because ACE is predominantly localized in the luminal plasma membrane of the endothelial cell, ACE inhibitors can interfere in platelet-endothelium interaction. In addition, Scholkens dislcoses that ACE inhibition potentiates the action of bradykinin (a strong stimulator of prostacyclin release from endothelial cells) by inhibiting its degradation and ACE inhibitors, consequently, have an inhibitory effect on platelet aggregation.

Zorn, J. et al, "Prevention of Arteriosclerotic Lesions with Calcium Antagonists or Captopril in Different Rat Hypertension Models," J. Cardiovasc. Pharmacol. Vol. 12 (Suppl 6), 1988, discloses beneficial effects in mesenteric arteries atherosclerosis with captopril in spontaneous hypertensive Okamoto rats (SHRs), but not in salt-sensitive Dahl rats.

Someya, N. et al, "Suppressive Effect of Captopril on Platelet Aggregation in Essential Hypertension," J. Cardiovasc. Pharmacol. 6:840–843, 1984, discloses at page 840 that "hypertension is closely related to the genesis and progress of atherosclerosis," and that "platelet function plays an important role in atherosclerosis, with platelet dysfunction demonstrable in several vascular diseases. It has been reported that platelet aggregation is increased in hypertensives . . . " At page 842, it is indicated that the "data demonstrated the inhibition of platelet aggregation in vivo after administration of captopril to hypertensive subjects . . . " At page 843, it is indicated that "platelet aggregability is greater in hypertensives than in normotensives . . . platelet abnormalities may be a risk factor in atherosclerosis . . . If captopril possesses an antiplate aggregability effect in addition to its hypotensive effect, it may be very useful for the prevention of atherosclerosis and thrombotic diseases associated with hypertension." Mizuno, K. et al "The effects of the angiotensin I-converting enzyme inhibitor, captopril, on serum lipoperoxides level and the renin-angiotensinaldosterone and kallikrein-kinin systems in hypertensive patients," Nippon Naibunpi Gakkai Zasshi, Feb. 20, 1984, discloses that captopril is a beneficial antihypertensive agent for preventing serum lipoperoxides concentration (LPX)-induced atherosclerosis in hypertensive patients.

Mizuno, K. et al "Acute effects of captopril on serum lipid peroxides level in hypertensive patients," Tohoku J. Exp. Med., May, 1984, 143(1) p. 127–8, suggests that inhibition of angiotensinconverting enzyme by captopril offers a possible therapeutic approach to the treatment of atherosclerosis complicated with hypertension.

The role of the renin-angiotensin system in atherosclerosis is not clear. Campbell-Boswell & Robertson, Exp. and Mol. Pathol. 35:265 (1981) reported that angiotensin II stimulated proliferation of isolated human vascular smooth muscle cells while Geisterfer et al, Circ. Res. 62: 749–756 (1988) showed no proliferation (but stimulation of growth) of isolated rat vascular smooth muscle cells.

Overturf, M. et al, Atherosclerosis, 59:383–399, 1986, discloses that studies with ACE inhibitors in cholesterol fed rabbits show no significant effects in the development of atherosclerosis.

Cecil, Textbook of Medicine, 16 Ed., pp 239 to 241, indicates at page 240 that blood pressure is an accelerator of atherosclerosis.

U.S. Pat. Nos. 4,046,889 and 4,105,776 to Ondetti et al disclose proline derivatives, including captopril, which are angiotensin converting enzyme (ACE) inhibitors useful for treating hypertension.

U.S. Pat. No. 4,337,201 to Petrillo discloses phosphinylalkanoyl substituted prolines, including fosinopril, which are ACE inhibitors useful for treating hypertension.

U.S. Pat. No. 4,374,829 discloses carboxyalkyl dipeptide derivatives, including enalapril, which are ACE inhibitors useful for treating hypertension.

U.S. Pat. No. 4,452,790 to Karanewsky et al discloses phosphonate substituted amino or imino acids and salts thereof and covers (S)-1-[6-amino-2-[[hydroxy(4-phenylbutyl)phosphinyl]-oxy]-1-oxohexyl]-L-proline (SQ 29,852, ceranapril). These compounds are ACE inhibitors useful in treating hypertension.

U.S. Pat. No. 4,316,906 to Ondetti et al discloses ether and thioether mercaptoacyl prolines which are ACE inhibitors useful in treating hypertension. This Ondetti et al patent covers zofenopril.

There are several different classes of compounds which have serum cholesterol lowering properties. Some of these compounds are inhibitors of the enzyme HMG CoA reductase which is essential in the production of cholesterol, such as mevastatin (disclosed in U.S. Pat. No. 3,983,140), lovastatin also referred to as mevinolin (disclosed in U.S. Pat. No. 4,231,938), pravastatin (disclosed in U.S. Pat. No. 4,346,227) and velostatin also referred to as synvinolin (disclosed in U.S. Pat. Nos. 4,448,784 and 4,450,171).

Other compounds which lower serum cholesterol may do so by an entirely different mechanism than the HMG CoA reductase inhibitors. For example, serum cholesterol may be lowered through the use of bile acid sequestrants such as cholestyramine, colestipol, DEAE-Sephadex and poly (diallylmethylamine) derivatives (such as disclosed in U.S. Pat. Nos. 4,759,923 and 4,027,009) or through the use of antihyperlipoproteinemics such as probucol and gemfibrozil which apparently lower serum "low density lipoproteins" (LDL) and/or converts LDL into high density lipoproteins (HDL).

U.S. Pat. No. 4,759,923 mentioned above discloses that poly(diallylmethylamine) derivatives which are bile salt sequestrants may be used in conjunction with drugs which reduce serum cholesterol by mechanisms other than sequestration, such as clofibrate, nicotinic acid, probucol, neomycin, p-aminosalicylic acid or mevinolin (also referred to as lovastatin).

Squalene synthetase is a microsomal enzyme which catalyzes the reductive dimerization of two molecules of farnesyl pyrophosphate (FPP) in the presence of nicotinamide adenine dinucleotide phosphate (reduced form) (NADPH) to form squalene (Poulter, C. D.; Rilling, H. C., in "Biosynthesis of Isoprenoid Compounds", Vol. I, Chapter 8, pp. 413–441, J. Wiley and Sons, 1981 and references therein). This enzyme is the first committed step of the de novo cholesterol biosynthetic pathway. The selective inhibition of this step should allow the essential pathways to isopentenyl tRNA, ubiquinone, and dolichol to proceed unimpeded. Squalene synthetase, along with HMG-CoA reductase has been shown to be down-regulated by receptor mediated LDL uptake (Faust, J. R.; Goldstein, J. L.; Brown, M. S. *Proc. Nat. Acad. Sci. USA,* 1979, 76, 5018–5022), lending credence to the proposal that inhibiting squalene synthetase will lead to an up-regulation of LDL receptor levels, as has been demonstrated for HMG-COA reductase, and thus ultimately should be useful for the treatment and prevention of hypercholesterolemia and atherosclerosis.

One approach to inhibitors of squalene synthetase is to design analogs of the substrate FPP. It is clear from the literature that the pyrophosphate moiety is essential for binding to the enzyme. However, such pyrophosphates are unsuitable as components of pharmacological agents due to their chemical and enzymatic lability towards allylic C—O cleavage, as well as their susceptibility to metabolism by phosphatases.

P. Ortiz de Montellano et al in *J. Med. Chem.,* 1977, 20, 243–249 describe the preparation of a series of substituted terpenoid pyrophosphates (Table A), and have shown these to be competitive inhibitors of the squalene synthetase enzyme. These substances retain the unstable allylic pyrophosphate moiety of FPP.

TABLE A

| No. | X | Y | Z |
|---|---|---|---|
| 1 | $CH_3$ | $CH_3$ | H |
| 2 | H | H | H |
| 3 | $C_2H_5$ | H | H |
| 4 | I | H | H |
| 5 | H | I | H |
| 6 | $CH_3$ | H | $SCH_3$ |

Corey and Volante, *J. Am. Chem. Soc.* 1976, 98, 1291–3, have prepared FPP analog A and presqualene pyrophosphate (PSQ—PP) analog B as inhibitors of squalene biosynthesis. (Presqualene pyrophosphate is an intermediate in the conversion of FPP to squalene). These inhibitors possess methylene groups in place of the allylic oxygen moiety of FPP and PSQ—PP, but still retain the chemically and enzymatically unstable pyrophosphate linkage.

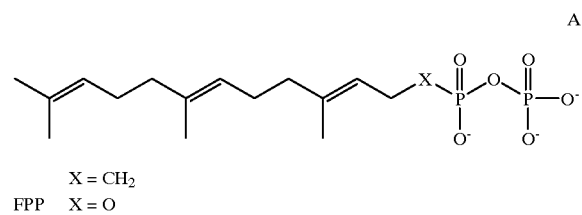

$X = CH_2$
FPP  $X = O$

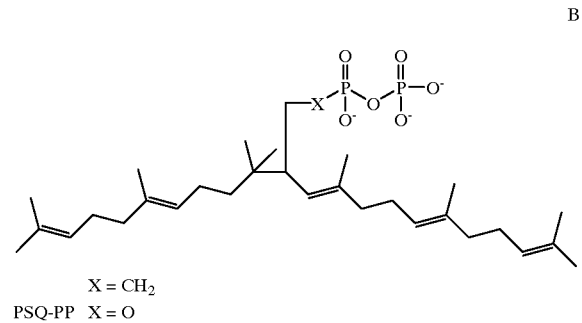

$X = CH_2$
PSQ-PP  $X = O$

Poulter and co-workers have prepared cyclopropane C (Sandifer, R. M., et al., *J. Am. Chem. Soc.* 1982, 104, 7376–8) which in the presence of inorganic pyrophosphate is an intermediate analog inhibitor of the enzyme squalene synthetase.

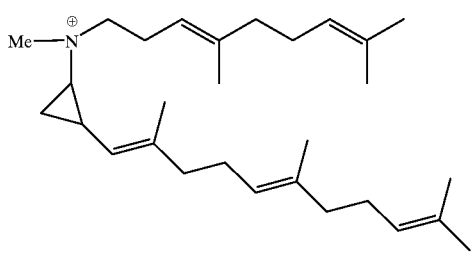

C

Altman and co-workers, Bertolino, A., et al., *Biochim. Biophys. Acta.* 1978, 530, 17–23, reported that farnesyl amine and related derivatives D inhibit squalene synthetase, but provide evidence that this inhibition is non-specific and probably related to membrane disruption.

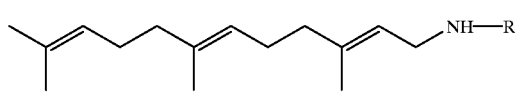

D

R = H, CH$_2$CH$_2$OH, CH$_2$CH$_2$OCH$_3$

Poulter, C. D., et al, *J. Org. Chem.*, 1986, 51, 4768, prepared compound E in a demonstration of a synthetic method, but did not report any biological data.

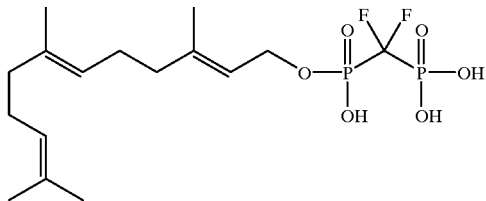

E

Poulter, C. D., Stremler, K. E., *J.A.C.S.*, 1987, 109, 5542 describes the synthesis and biological evaluation of compounds having structure F. These compounds were evaluated as alternative substrates for avian liver farnesyl diphosphate and lemon peel cyclase.

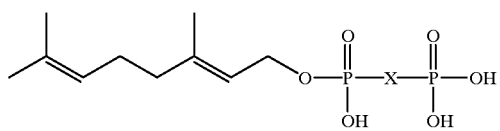

F

X = CH$_2$, CF$_2$

McClard, R. W. and Poulter, C. D., et al., *J.A.C.S.* 1987, 109, 5544, reported that phosphinylphosphonates G and H were competitive inhibitors of the 1'-4-condensation between isopentenyl diphosphate and geranyl diphosphate catalyzed by avian liver farnesyl diphosphate synthetase. Phosphinylphosphonates G and H had Ki's of 19 $\mu$M and 71 $\mu$M, respectively. They also reported the speculative isolation of the farnesyl phosphinylphosphonate I, and the geranyl phosphinylphosphonate J from the enzymatic reaction of G with geranyl pyrophosphate or dimethylallyl pyrophosphate, respectively. The structures of I and J were tentatively assigned based on relative TLC mobilities. They hypothesized that I could be a potential inhibitor of squalene synthetase.

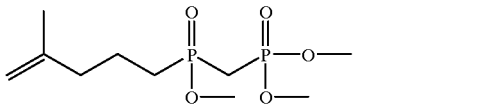

G

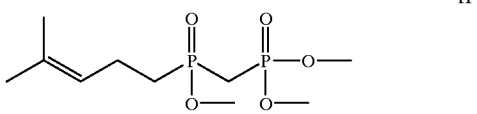

H

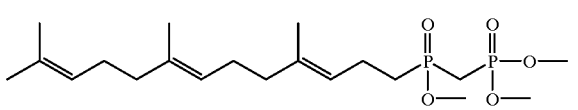

I

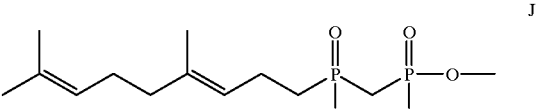

J

Capson, T. L., PhD dissertation, June 1987, Dept. of Medicinal Chemistry, the University of Utah, Abstract, Table of Contents, pp. 16, 17, 40–43, 48–51, Summary, discloses cyclopropanes of the structure discloses cyclopropanes of the structure

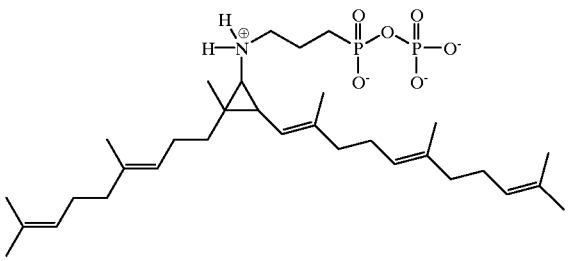

as intermediate analog inhibitors of squalene synthetase.

S. A. Biller et al., Journal of Medicinal Chemistry, 1988, Vol. 31, No. 10, pp 1869 to 1871 disclose that isoprenoid (phosphinylmethyl) phosphonates (PMPs) inhibit squalene synthetase. These phosphonates have the structures

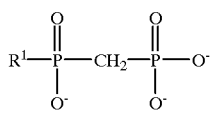

2a–d

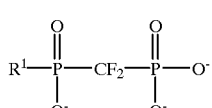

3a, b

R$^1$ a

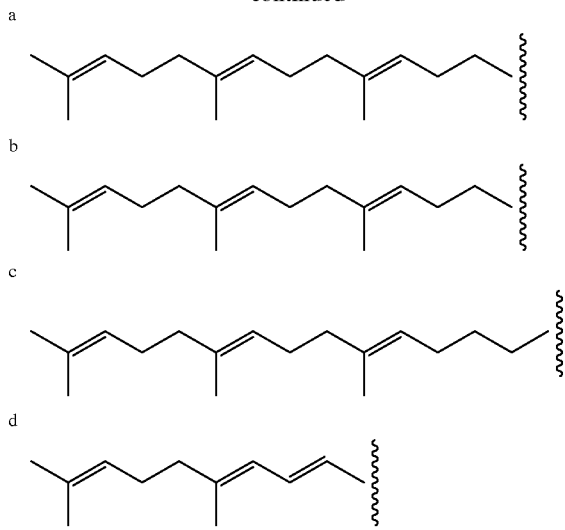

b c d

U.S. Pat. Nos. 4,871,721 and 4,924,024 disclose phosphorus-containing squalene synthetase inhibitors of the structure

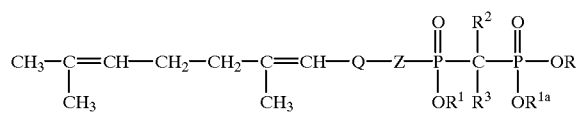

wherein Q is

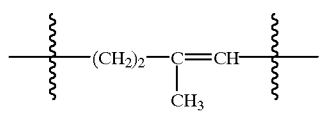

or a bond;

Z is —$(CH_2)_n$— or —$(CH_2)_p$—CH=CH—$(CH_2)_m$—, wherein n is 1 to 5; p is 0, 1 or 2; m is 0, 1 or 2;

R, $R^1$ and $R^{1a}$ may be the same or different and are H, lower alkyl or a metal ion; and $R^2$ and $R^3$ may be the same or different and are H or halogen.

DESCRIPTION OF THE INVENTION

In accordance with the present invention, a method is provided for preventing, stabilizing or causing regression of atherosclerosis employing a cholesterol lowering drug, which is preferably an inhibitor of the enzyme 3-hydroxy-3-methylglutaryl coenzyme A (HMG CoA) reductase, in combination with an angiotensin-converting enzyme (ACE) inhibitor, wherein a therapeutically effective amount of the above type compounds is systemically, such as orally or parenterally, administered over a prolonged period.

In addition, in accordance with the present invention, a new combination of drugs is provided which is effective for use in the method of the present invention and includes an HMG CoA reductase inhibitor which is pravastatin or (S)-4-[[[1-(4-fluorophenyl)-3-(1-methylethyl)-1H-indol-2-yl] ethynyl]hydroxyphosphinyl]-3-hydroxy-butanoic acid, disodium salt (SQ 33,600) or dilithium salt, and an ACE inhibitor.

The phrase "stabilizing" atherosclerosis as used herein refers to slowing down the development of atherosclerosis and/or inhibiting formation of new atherosclerotic lesions.

The phrase "causing regression of" atherosclerosis as used herein refers to reducing and/or eliminating atherosclerotic lesions.

The combination of the cholesterol lowering drug and ACE inhibitor will be employed in a weight ratio to each other of within the range of from about 0.001:1 to about 1000:1 and preferably from about 0.05:1 to about 100:1.

The removal of multiple atherogenic stimuli by administration of an appropriate drug combination in accordance with the present invention is of greater therapeutic benefit than monotherapy. In addition, significantly lower doses of the individual components of an appropriate drug combination will be necessary to produce a desired therapeutic effect than would be needed if specified components of the combination were used alone. Thus, by reducing the dosage of individual agents comprising the therapeutic combination, the potential for producing drug-specific side effects in patients is minimized, particularly if components of the combination have different pharmacologic mechanisms of action. It is believed that the combination employed in the method of the invention in which component drugs have separate mechanisms of action, will produce a maximum therapeutic effect which is greater than can be achieved by same drugs when given alone, even at maximum tolerated doses.

Cholesterol lowering drugs or drugs which are inhibitors of cholesterol biosynthesis which may be used in the method of the invention include HMG CoA reductase inhibitors, squalene synthetase inhibitors, fibric acid derivatives, bile acid sequestrants, probucol, niacin and the like.

The HMG CoA reductase inhibitors suitable for use herein include, but are not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, velostatin (synvinolin) and related compounds as disclosed in U.S. Pat. Nos. 4,448,784 and 4,450,171, with lovastatin, pravastatin or velostatin being preferred. Other HMG CoA reductase inhibitors which may be employed herein include, but are not limited to, fluindostatin (Sandoz XU-62–320), pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)alkyl]-pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-di-substituted pyrrole, furan and thiophene derivatives as disclosed in European Patent Application No. 0221025, naphthyl analogs of mevalonolactone as disclosed in U.S. Pat. No. 4,686,237, octahydro-naphthalenes such as disclosed in U.S. Pat. No. 4,499,289, keto analogs of mevinolin (lovastatin) as disclosed in European Patent Application No. 0,142,146 A2, as well as other known HMG CoA reductase inhibitors.

In addition, phosphinic acid compounds useful in inhibiting HMG CoA reductase suitable for use herein are disclosed in GB 2205837 which compounds have the moiety

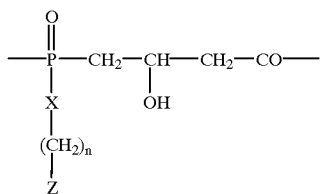

wherein X is —O— or —NH—, n is 1 or 2 and Z is a hydrophobic anchor.

Examples of such compounds include (S)-4-[[[4'-fluoro-3,3',5-trimethyl[1,1'-biphenyl]-2-yl]-methoxy]methoxyphosphinyl]-3-hydroxy-butanoic acid, methyl ester or its monolithium salt, (S)-4-[[[4'-fluoro-3,3',5-trimethyl[1,1'-biphenyl]-2-yl]methoxy]hydroxyphosphinyl]-3hydroxybutanoic acid, dilithium salt, (3S)-4-[[[4'-fluoro-3,3',5-trimethyl[1,1'-biphenyl]-2-yl]methoxy]methylphosphinyl]-3-hydroxybutanoic acid, monolithium salt, (S)-4-[[[2,4-dichloro-6-[(4-fluorophenyl)-methoxy]phenyl]methoxy]methoxyphosphinyl]-3hydroxybutanoic acid, monolithium salt, (3S)-4-[[[2,4-dichloro-6-[(4-fluorophenyl)-methoxy]phenyl]methoxy]hydroxyphosphinyl]-3-hydroxybutanoic acid, dilithium salt, (3S)-4-[[2,4-dichloro-6-[(4-fluorophenyl)-methoxy]phenyl]methoxy]methylphosphinyl]-3-hydroxybutanoic acid, or its methyl ester, and (S)-4-[[[[4'-fluoro-3,3',5-trimethyl[1,1'-biphenyl-2-yl]methyl]amino]methoxyphosphinyl]-3-hydroxybutanoic acid, monolithium salt.

Another class of HMG CoA reductase inhibitors suitable for use herein include phosphinic acid compounds disclosed in GB 2205838, which compounds have the moiety

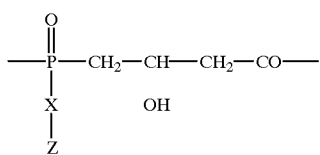

wherein X is —CH₂— —CH₂—CH₂—, —CH═CH—, —Ch₂CH₂CH₂—, —C≡C— or —CH₂O—, where O is linked to Z, and Z is a hydrophobic anchor.

Examples of such compounds include (S)-4-[[[1-(4-fluorophenyl)-3-(1-methylethyl)-1H-indol-2-yl]ethynyl]hydroxyphosphinyl]-3-hydroxyfutanoic acid, or its sodium salt (SQ 33,600) (preferred) or its dilithium salt;

(S)-4-[[(E)-2-[4'-fluoro-3,3',5-trimethyl-[1,1'-biphenyl]-2-yl]ethenyl]hydroxyphosphinyl]-3-hydroxybutanoic acid or its dilithium salt;

(S)-4-[[2-[4'-fluoro-3,3',5-trimethyl-[1,1'-biphenyl]-2-yl]ethyl]hydroxyphosphinyl]-3-hydroxybutanoic acid, methyl ester or mono- or di-alkali metal salts thereof;

(S)-4-[[[4'-fluoro-3,3',5-trimethyl-[1,1'-biphenyl]-2-yl]ethynyl]methoxyphosphinyl]-3-hydroxybutanoic acid or the methyl ester thereof;

(5Z)-4-[[2-[4'-fluoro-3,3',5-trimethyl-[1,1'-biphenyl]-2-yl]ethenyl]hydroxyphosphinyl]-3-hydroxybutanoic acid, methyl esters thereof;

(S)-4-[[2-3-(4-fluorophenyl)-1-(1-methyl-ethyl)-1H-indol-2-yl]ethyl]methoxyphosphinyl]-3-hydroxybutanoic acid, methyl esters;

(S)-4-[[2-[[1,1'-biphenyl]-2-yl]ethyl]-methoxyphosphinyl-3-hydroxybutanoic acid, methyl ester;

(S)-4-[[2-[4'-fluoro-3,3',5-trimethyl-[1,1'-biphenyl]-2-yl]ethyl]hydroxyphosphinyl]-3-hydroxybutanoic acid, dilithium salt;

(S)-4-[[2-[4'fluoro-3,3¹,5-trimethyl-[1,1'-biphenyl]-2-yl]ethynyl]hydroxyphosphinyl]-3-hydroxybutanoic acid, dilithium salt;

(SZ)-4-[[2-[4'-fluoro-3,3',5-trimethyl-[1,1'-biphenyl]-2-yl]ethenyl]hydroxyphosphinyl]-3-hydroxybutanoic acid, dilithium salt;

(S)-4-[[2-[3-(4-fluorophenyl)-1-(1-methyl-ethyl)-1H-indol-2-yl]ethyl]hydroxyphosphinyl]-3-hydroxybutanoic acid, dilithium salt;

(S)-4-[[2-[(1,1'-biphenyl]-2-yl]ethyl]hydroxyphosphinyl]-3-butanoic acid, dilithium salt;

(S)-4-(hydroxymethoxyphosphinyl)-3-[[(1,1dimethylethyl)diphenylsilylloxy]butanoic acid, methyl ester, or its dicyclohexylamine (1:1) salt;

(S)-4-[[2-[1-(4-fluorophenyl)-3-(1-methyl-ethyl)-1-indol-2-yl]ethynyl]hydroxyphosphinyl]-3-hydroxybutanoic acid or its dilithium salt or disodium salt or methyl ester thereof;

(E)-4-[[2-[3-(4-fluorophenyl)-1-(1-methyl-ethyl)-1H-indol-2-yl]ethenyl]hydroxyphosphinyl]-3-hydroxybutanoic acid or its dilithium salt or methyl ester thereof;

4-[[2-[4'-fluoro-3,3',5-trimethyl[1,1'-biphenyl]-2-yl]ethyl]hydroxyphosphinyl]-3-hydroxy-butanoic acid or its dilithium salt or methyl ester thereof;

(E)-4-[[2-[4'-fluoro-3,3',5-trimethyl[1,1'-biphenyl]-2-yl]ethenyl]hydroxyphosphinyl]-3-hydroxybutanoic acid or its dilithium salt or methyl ester thereof;

(S)-4-[[[2,4-dimethyl-6-[(4-fluorophenyl)-methoxy]phenyl]ethyl]hydroxyphosphinyl]-3-hydroxybutanoic acid or its dilithium salt or methyl ester thereof;

(S)-4-[[[2,4-dimethyl-6-[(4-fluorophenyl)-methoxy]phenyl]ethynyl]hydroxyphosphinyl]-3-hydroxybutanoic acid or its dilithium salt or methyl ester thereof;

(S)-4-[[2-[3,5-dimethyl[1,1'-biphenyl])-2-yl]ethyl)hydroxyphosphinyl]-3-hydroxybutanoic acid or its dilithium salt or methyl ester thereof;

(S)-4-[[2-[4'-fluoro-3,5-dimethyl[1,1'-biphenyl]-2-yl]ethyl]hydroxyphosphinyl]-3-hydroxybutanoic acid or its dilithium salt or methyl ester thereof;

(S)-4-[[2-[[1,1'-biphenyl]-2-yl]ethynyl]-hydroxyphosphinyl]-3-hydroxybutanoic acid or its dilithium salt or methyl ester thereof;

(S)-4-[[2-(5-(4-fluorophenyl)-3-(1-methyl-ethyl)-1-phenyl-1H-pyrazol-4-yl]ethynyl]methoxy-phosphinyl]-3-hydroxybutanoic acid, methyl ester;

(S)-4-[[2-[1-(4-fluorophenyl)-3-(1-methyl-ethyl)-1H-indol-2-yl]ethyl]hydroxyphosphinyl]-3-hydroxybutanoic acid or its dilithium salt or methyl ester thereof;

(S)-4-[[2-[5-(4-fluorophenyl)-3-(1-methyl-ethyl)-1-phenyl-1H-pyrazol-4-yl]ethynyl]hydroxy-phosphinyl]-3-hydroxybutanoic acid, dilithium salt;

(E)-4-[[2-[5-(4-fluorophenyl)-3-(1-methyl-ethyl)-1-phenyl-1H-pyrazol-4-yllethenyl]methoxy-phosphinyl]-3-hydroxybutanoic acid, methyl ester;

(E)-4-[[2-[5-(4-fluorophenyl)-3-(1-methyl-ethyl)-1-phenyl-1H-pyrazol-4-yl]ethenyl]hydroxy-phosphinyl]-3-hydroxybutanoic acid, dilithium salt;

(S)-4-[[2-[5-(4-fluorophenyl)-3-(1-methyl-ethyl)-1-phenyl-1H-pyrazol-4-yl]ethyl]methoxy-phosphinyl]-3-hydroxybutanoic acid, methyl ester;

(S)-4-[[2-[5-(4-fluorophenyl)-3-(1-methyl-ethyl)-1-phenyl-1H-pyrazol-4-yl]ethyl]hydroxy-phosphinyl]-3-hydroxybutanoic acid, dilithium salt;

(S)-4-[[2-[3-(4-fluorophenyl)-5-(1-methyl-ethyl)-1-phenyl-1H-pyrazol-4-yl]ethyl]methoxy-phosphinyl]-3-hydroxybutanoic acid, methyl ester;

(S)-4-[[2-[3-(4-fluorophenyl)-5-(1-methyl-ethyl)-1-phenyl-1H-pyrazol-4-yl]ethyl]hydroxy-phosphinyl]-3-hydroxybutanoic acid, dilithium salt;

(S)-4-[[2-[3-(4-fluorophenyl)-5-(1-methyl-ethyl)-1-phenyl-1H-pyrazol-4-yl]ethynyl]methoxy-phosphinyl]-3-hydroxybutanoic acid, methyl ester;

(S)-4-[[2-[3-(4-fluorophenyl)-5-(1-methyl-ethyl)-1-phenyl-1H-pyrazol-4-yl]ethynyl]hydroxy-phosphinyl]-3-hydroxybutanoic acid, dilithium salt;

(S)-4-[[[4-(4-fluorophenyl)-1-(1-methyl-ethyl)-3-phenyl-1H-pyrazol-5-yl]ethynyl]methoxy-phosphinyl]-3-hydroxybutanoic acid, methyl ester;

(S)-4-[[[4-(4-fluorophenyl)-1-(1-methyl-ethyl)-3-phenyl-1H-pyrazol-5-yl]ethynyl]hydroxy-phosphinyl]-3-hydroxybutanoic acid, dilithium salt;

(S)-4-[[2-[4-(4-fluorophenyl)-1-(1-methyl-ethyl)-3-phenyl-1H-pyrazol-5-yl]ethyl]methoxy-phosphinyl]-3-hydroxybutanoic acid, methyl ester;

(S)-4-[[2-[4-(4-fluorophenyl)-1-(1-methyl-ethyl)-3-phenyl-1H-pyrazol-5-yl]ethyl]hydroxy-phosphinyl]-3-hydroxybutanoic acid, dilithium salt;

(S)-4-[[[1-(4-fluorophenyl)-4-(1-methyl-ethyl)-2-phenyl-1H-imidazole-5-yl]ethynyl]methoxy-phosphinyl]-3-hydroxybutanoic acid, methyl ester;

(S)-4-[[[1-(4-fluorophenyl)-4-(1-methyl-ethyl)-2-phenyl-1H-imidazol-5-yl]ethynyl]methoxy-phosphinyl]-3-hydroxybutanoic acid, methyl ester;

(S)-4-[[2-[1-(4-fluorophenyl)-4-(1-methyl-ethyl)-2-phenyl-1H-imidazol-5-yl]ethyl]methoxy-phosphinyl]-3-hydroxybutanoic acid, methyl ester;

(S)-4-[[2-[1-(4-fluorophenyl)-4-(1-methyl-ethyl)-2-phenyl-1H-imidazol-5-yl]ethyl]hydroxy-phosphinyl]-3-hydroxybutanoic acid, dilithium salt;

(S)-4-[[[2-(cyclohexylmethyl)-4,6-dimethyl-phenyl]ethynyl]hydroxyphosphinyl]-3-hydroxybutanoic acid or its dilithium salt or methyl ester thereof;

4-[[2-[2-(cyclohexylmethyl)-4,6-dimethyl-phenyl]ethenyl]hydroxyphosphinyl]-3-hydroxybutanoic acid or its dilithium salt or methyl ester thereof;

(S)-4-[[2-[2-(cyclohexylmethyl)-4,6-dimethyl-phenyl]ethyl]hydroxyphosphinyl]-3-hydroxybutanoic acid or its dilithium salt or methyl ester thereof;

4-[[[[4'-fluoro-3,3',5-trimethyl[1,1'-biphenyl]-2-yl]oxy]methyl]hydroxyphosphinyl]-3hydroxybutanoic acid or its dilithium salt or methyl ester thereof;

4-[[[4'-fluoro-3,3',5-trimethyl[1,1'biphenyl]-2-yl]methyl]hydroxyphosphinyl]-3-hydroxy-butanoic acid or its dilithium salt or methyl ester thereof;

(S)-4-[[[1-(4-fluorophenyl)-3-methyl-2-naphthalenyl]ethynyl]hydroxyphosphinyl]-3-hydroxy-butanoic acid or its dilithium salt or methyl ester thereof;

(E)-4-[[2-[1-(4-fluorophenyl)-3-methyl-2-naphthalenyl]ethenyl]hydroxyphosphinyl]-3-hydroxy-butanoic acid or its dilithium salt or methyl ester thereof;

(S)-4-[[2-[1-(4-fluorophenyl)-3-methyl-2-naphthalenyl]ethyl]hydroxyphosphinyl]-3-hydroxy-butanoic acid or its dilithium salt or methyl ester thereof;

4-[[3-[4'-fluoro-3,3',5-trimethyl[1,1'-biphenyl]-2-yl]propyl]methoxyphosphinyl]-3hydroxybutanoic acid, methyl ester;

4-[[3-[4'-fluoro-3,3',5-trimethyl[1,1'-biphenyl]-2-yl]propyl]hydroxyphosphinyl]-3hydroxybutanoic acid, dilithium salt;

[1S-[1α(R*),2α,4αβ,8β,8aα]]-4-[[2-[8-(2,2-dimethyl-1-oxobutoxy)decahydro-2-methyl-1-naphthalenyl]ethyl]rnethoxyphosphinyl]-3-hydroxy-butanoic acid, methyl ester;

[1S-[1α(R*),2α,4αβ,8β,8αβ]]-4-[[2-[8-(2,2-dimethyl-1-oxobutoxy)decahydro-2-methyl-1-naphthalenyl]ethyl]hydroxyphosphinyl]-3-hydroxy-butanoic acid, dilithium salt;

(S)-4-[[[3'-(4-fluorophenyl)spiro]cyclo-pentane-1,1'-[1H]indene]-2-yl]ethynyl]methoxyphos-phinyl]-3-hydroxybutanoic acid, methyl ester; and (S)-4-[[[3'-(4-fluorophenyl)spiro]cyclo-pentane-1,1'-[1H]indene]-2-yl]ethynyl]hydroxyphos- phinyl]-3-hydroxybutanoic acid, dilithium salt.

The squalene synthetase inhibitors suitable for use herein include, but are not limited to, those disclosed by Biller et al., supra, including isoprenoid (phosphinylmethyl) phosphonates such as those of the formula

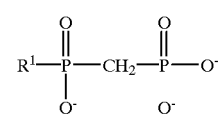

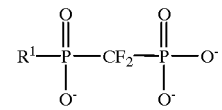

R$^1$ a
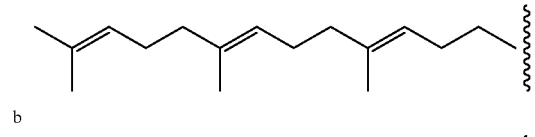

b
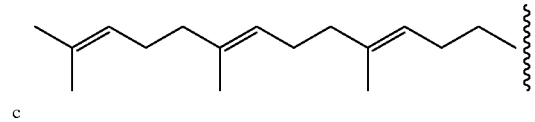

c

d
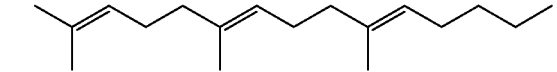

including the triacids thereof, triesters thereof and tripotassium and trisodium salts thereof as well as other squalene synthetase inhibitors disclosed in pending U.S. Pat. Nos. 4,871,721 and 4,924,024 and in Biller et al, J. Med. Chem., 1988, Vol. 31, No. 10, pp 1869 to 1871.

In addition, other squalene synthetase inhibitors suitable for use herein include the terpenoid pyrophosphates disclosed by P. Ortiz de Montellano et al., J. Med. Chem.; 1977, 20, 243–249, the farnesyl diphosphate analog A and presqualene pyrophosphate (PSQ-PP) analogs as disclosed by Corey and Volante, J. Am. Chem. Soc. 1976, 98, 1291–1293, phosphinylphosphonates reported by McClard, R. W. et al., J.A.C.S., 1987, 109, 5544 and cyclopropanes reported by Capson, T. L., PhD dissertation, June, 1987, Dept. Med. Chem. U. of Utah, Abstract, Table of Contents, pp. 16, 17, 40–43, 48–51, Summary.

Preferred are pravastatin, lovastatin or velostatin or a squalene synthetase inhibitor such as disclosed by Biller et al., supra or combinations thereof which include a weight ratio of the HMG CoA reductase inhibitor:squalene synthetase inhibitor of from about 0.05:1 to about 100:1.

Other cholesterol lowering drugs which function other than by inhibiting the enzyme HMG CoA reductase or squalene synthetase suitable for use herein include, but are not limited to, antihyperlipoproteinemic agents such as fibric acid derivatives, such as fenofibrate, gemfibrozil, clofibrate, bezafibrate ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (Secholex®, Polidexide®), as well as clofibrate, lipostabil (Rhone-Poulenc), Eisai E-5050 (an N-substituted ethanolamine derivative), imanixil (HOE-402) tetrahydrolipstatin (THL), istigmastanylphosphorylcholine (SPC, Roche), aminocyclodextrin (Tanabe Seiyoku), Ajinomoto AJ-814 (azulene derivative), melinamide (Sumitomo), Sandoz 58–035, American Cyanamid CL-277,082 and CL-283,546 (disubstituted urea derivatives), nicotinic acid, neomycin, p-aminosalicylic acid, aspirin, poly-(diallylmethylamine) derivatives such as disclosed in U.S. Pat. No. 4,759,923, quaternary amine poly(diallyldimethylammonium chloride) and ionenes such as disclosed in U.S. Pat. No. 4,027,009, and other known serum cholesterol lowering agents which lower cholesterol through a mechanism other than by the inhibition of the enzyme HMG CoA reductase or squalene synthetase.

Also preferred are combinations of any of the HMG CoA reductase inhibitors, preferably pravastatin, or isoprenoid (phosphinylmethyl) phosphonates disclosed by Biller et al., supra, gemfibrozil or fenofibrate.

The angiotensin converting enzyme inhibitor which may be employed herein preferably includes those containing a mercapto (—S—) moiety such as substituted proline derivatives, such as any of those disclosed in U.S. Pat. No. 4,046,889 to Ondetti et al mentioned above, with captopril, that is, 1-[(2S)-3-mercapto-2-methylpropionyl]-L-proline, being preferred, and mercaptoacyl derivatives of substituted prolines such as any of those disclosed in U.S. Pat. No. 4,316,906 with zofenopril being preferred.

Other examples of mercapto containing ACE inhibitors that may be employed herein include rentiapril (fentiapril, Santen) disclosed in Clin. Exp. Pharmacol. Physiol. 10:131 (1983); as well as pivopril, that is

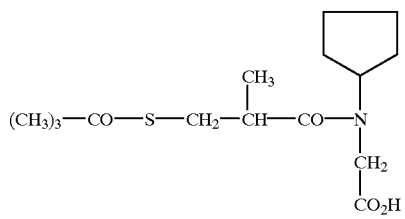

and YS980, that is

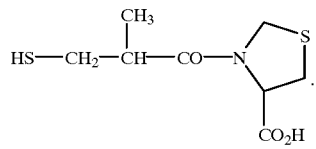

Other examples of angiotensin converting enzyme inhibitors which may be employed herein include any of those disclosed in U.S. Pat. No. 4,374,829 mentioned above, with N-(1-ethoxycarbonyl-3-phenylpropyl)-L-alanyl-L-proline, that is, enalapril, being preferred, any of the phosphonate substituted amino or imino acids or salts disclosed in U.S. Pat. No. 4,452,790 with (S)-1-[6-amino-2-[[hydroxy-(4-phenylbutyl)-phosphinyl]oxy]-1-oxohexyl]-L-proline (SQ 29,852 or ceranapril) being preferred, phosphinylalkanoyl prolines disclosed in U.S. Pat. No. 4,168,267 mentioned above with fosinopril being preferred, any of the phosphinylalkanoyl substituted prolines disclosed in U.S. Pat. No. 4,337,201, and the phosphonamidates disclosed in U.S. Pat. No. 4,432,971 discussed above.

Other examples of ACE inhibitors that may be employed herein include Beecham's BRL 36,378 as disclosed in European patent Nos. 80822 and 60668; Chugai's MC-838 disclosed in CA. 102:72588v and Jap. J. Pharmacol. 40:373 (1986); Ciba-Geigy's CGS 14824 (3-([1-ethoxycarbonyl-3-phenyl-(1S)-propyl]-amino)-2,3,4,5-tetrahydro-2-oxo-1-(3S)-benzazepine-1 acetic acid HCl) disclosed in U.K. Patent No. 2103614 and CGS 16,617 (3(S)-[[(1S)-5-amino-1-carboxypentyl]amino]-2,3,4,5-tetrahydro-2-oxo-1H-1-benzazepine-1-ethanoic acid) disclosed in U.S. Pat. No. 4,473,575; cetapril (alacepril, Dainippon) disclosed in Eur. Therap. Res. 39:671 (1986); 40:543 (1986); ramipril (Hoechst) disclosed in Eur. Patent No. 79-022 and Curr. Ther. Res. 40:74 (1986); Ru 44570 (Hoechst) disclosed in Arzneimittelforschung 35:1254 (1985), cilazapril (Hoffman-LaRoche) disclosed in J. Cardiovasc. Pharmacol. 9:39 (1987); $R_0$31–2201 (Hoffman-LaRoche) disclosed in FEBS Lett. 165:201 (1984); lisinopril (Merck) disclosed in Curr. Therap. Res. 37:342 (1985) and Eur. patent appl. No. 12-401, indalapril (delapril) disclosed in U.S. Pat. No. 4,385,051; indolapril (Schering) disclosed in J. Cardiovasc. Pharmacol. 5:643, 655 (1983); spirapril (Schering) disclosed in Acta. Pharmacol. Toxicol. 59 (Supp. 5):173 (1986); perindopril (Servier) disclosed in Eur. J. Clin. Pharmacol. 31:519 (1987); quinapril (Warner-Lambert) disclosed in U.S. Pat. No. 4,344,949 and CI 925 (Warner-Lambert) ([3S-[2[R(*)R(*)I]]3R(*)]-2-[2-[[1-(ethoxycarbonyl)-3-phenylpropyl]amino[-1-oxopropyl]-1,2,3,4-tetrahydro-6,7-dimethoxy-3-isoquinoline-carboxylic acid HCl) disclosed in Pharmacologist 26:243, 266 (1984), WY-44221 (Wyeth) disclosed in J. Med. Chem. 26:394 (1983).

Preferred are those ACE inhibitors which are proline or substituted proline derivatives and most preferred are such ACE inhibitors which include a mercapto group.

The above-mentioned U.S. patents are incorporated herein by reference.

In carrying out the method of the present invention, the combination of the cholesterol lowering drug and ACE inhibitor may be administered to mammalian species, such as monkeys, dogs, cats, rats, humans, etc. and as such may be incorporated in a conventional systemic dosage form, such as a tablet, capsule, elixir or injectable. The above dosage forms will also include the necessary carrier material, excipient, lubricant, buffer, antibacterial, bulking agent (such as mannitol), anti-oxidants (ascorbic acid of sodium bisulfite) or the like. Oral dosage forms are preferred, although parenteral forms are quite satisfactory as well.

The dose administered must be carefully adjusted according to age, weight and condition of the patient, as well as the route of administration, dosage form and regimen and the desired result.

Thus, for oral administration, a satisfactory result may be obtained employing the HMG CoA reductase inhibitor in dosages employed, for example, for lovastatin as indicated in the Physician's Desk Reference, such as in an amount within the range of from about 1 to 2000 mg, and preferably from about 4 to about 200 mg. The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount of from about 0.1 to about 100 mg, preferably from about 5 to about 80 mg, and more preferably from about 10 to about 40 mg.

A preferred oral dosage form, such as tablets or capsules will contain the squalene synthetase inhibitor in an amount of from about 10 to about 500 mg, preferably from about 25 to about 200 mg.

The other serum cholesterol lowering drugs when present will be employed in dosages normally employed as indicated in the Physician's Desk Reference, for each of such agents such as in an amount within the range of from about 2 mg to about 7500 mg and preferably from about 2 mg to about 4000 mg.

With regard to the ACE inhibitor, for oral administration, a satisfactory result may be obtained employing the ACE inhibitor in an amount within the range of from about 0.01 mg/kg to about 100 mg/kg and preferably from about 0.1 mg/kg to about 5 mg/kg.

A preferred oral dosage form, such as tablets or capsules, will contain the ACE inhibitor in an amount of from about 0.1 to about 500 mg, preferably from about 2 to about 5 mg, and more preferably from about 1 to about 3 mg.

For parenteral administration, the ACE inhibitor will be employed in an amount within the range of from about 0.005 mg/kg to about 10 mg/kg and preferably from about 0.005 mg/kg to about 0.3 mg/kg.

The cholesterol lowering agent and ACE inhibitor may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

Tablets of various sizes can be prepared, e.g., of about 2 to 2000 mg in total weight, containing one or both of the active substances in the ranges described above, with the remainder being a physiologically acceptable carrier of other materials according to accepted pharmaceutical practice. These tablets can, of course, be scored to provide for fractional doses. Gelatin capsules can be similarly formulated.

Liquid formulations can also be prepared by dissolving or suspending one or the combination of active substances in a conventional liquid vehicle acceptable for pharmaceutical administration so as to provide the desired dosage in one to four teaspoonsful.

Such dosage forms can be administered to the patient on a regimen of one to four doses per day.

According to another modification, in order to more finely regulate the dosage schedule, the active substances may be administered separately in individual dosage units at the same time or carefully coordinated times. Since blood levels are built up and maintained by a regulated schedule of administration, the same result is achieved by the simultaneous presence of the two substances. The respective substances can be individually formulated in separate unit dosage forms in a manner similar to that described above.

Fixed combinations of cholesterol lowering drug and ACE inhibitor are more convenient and are preferred, especially in tablet or capsule form for oral administration.

In formulating the compositions, the active substances, in the amounts described above, are compounded according to accepted pharmaceutical practice with a physiologically acceptable vehicle, carrier, excipient, binder, preservative, stabilizer, flavor, etc., in the particular type of unit dosage form.

Illustrative of the adjuvants which may be incorporated in tablets are the following: a binder such as gum tragacanth, acacia, corn starch or gelatin; an excipient such as dicalcium phosphate or cellulose; a disintegrating agent such as corn starch, potato starch, alginic acid or the like; a lubricant such as stearic acid or magnesium stearate; a sweetening agent such as sucrose, aspartame, lactose or saccharin; a flavoring agent such as orange, peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup of elixir may contain the active compound, water, alcohol or the like as the carrier, glycerol as solubilizer, sucrose as sweetening agent, methyl and propyl parabens as preservatives, a dye and a flavoring such as cherry or orange.

Some of the active substances described: above form commonly known, pharmaceutically acceptable salts such as alkali metal and other common basic salts or acid addition salts, etc. References to the base substances are therefore intended to include those common salts known to be substantially equivalent to the parent compound.

The formulations as described above will be administered for a prolonged period, that is, for as long as the potential for arteriosclerosis remain or the symptoms continue. Sustained release forms of such formulations which may provide such amounts biweekly, weekly, monthly and the like may also be employed. A dosing period of at least one to two weeks are required to achieve minimal benefit.

EXAMPLE 1

A pravastatin formulation in the form of tablets having the following composition was prepared as described below.

| Ingredient | Parts by Weight |
| --- | --- |
| Pravastatin | 7 |
| Lactose | 67 |
| Microcrystalline cellulose | 20 |
| Croscarmellose sodium | 2 |
| Magnesium stearate | 1 |
| Magnesium oxide | 3 |

Pravastatin, magnesium oxide and a fraction (30%) of the lactose were mixed together for 2 to 10 minutes employing a suitable mixer. The resulting mixture was passed through a #12 to #40 mesh size screen. Microcrystalline cellulose, croscarmellose sodium and the remaining lactose were added and the mixture was mixed for 2 to 10 minutes. Thereafter, magnesium stearate was added and mixing was continued for 1 to 3 minutes.

The resulting homogeneous mixture was then compressed into tablets each containing 5 mg pravastatin.

A captopril formulation suitable for oral administration together with pravastatin is prepared as described below.

1000 tablets each containing 100 mg of 1-[(2S)-3-mercapto-2-methylpropionyl]-L-proline were produced from the following ingredients.

| | |
|---|---|
| 1-[(2S)-3-Mercapto-2-methylpropionyl]-L-proline (captopril) | 7 g |
| Corn starch | 50 g |
| Gelatin | 7.5 g |
| Avicel (microcrystalline cellulose) | 25 g |
| Magnesium stearate | 2.5 g |

The captopril and corn starch are admixed with an aqueous solution of the gelatin. The mixture is dried and ground to a fine powder. The Avicel and then the magnesium stearate are admixed with the granulation. This is then compressed in a tablet to form 1000 tablets each containing 7 mg of active ingredient.

The pravastatin tablets and captopril tablets may be administered as a combination in accordance with the teachings of the present invention to treat or prevent atherosclerosis. In addition, the pravastatin and captopril tablets may be ground up into powders and used together in a single capsule.

EXAMPLE 2

Pravastatin tablets are prepared employing conventional pharmaceutical techniques containing 20 mg pravastatin and inert ingredients employed in lovastatin tablets, namely cellulose, color, lactose, magnesium stearate and starch and butylated hydroxyanisole as a preservative as described in the 1990 PDR.

The pravastatin tablets may be employed in combination with enalapril tablets containing 7 mg enalapril and inactive ingredients as described in the 1990 PDR, in separate or combined dosage forms to treat or prevent atherosclerosis in accordance with the present invention.

EXAMPLE 3

Tablets containing 500 mg clofibrate and 5 mg enalapril and inactive ingredients as described in the 1990 PDR, may be employed in separate dosage forms or combined in a single capsule form to treat or prevent atherosclerosis in accordance with the present invention.

EXAMPLE 4 to 6

Combinations of ciprofibrate, bezafibrate, clinofibrate with captopril, ceranapril or fosinopril may also be prepared in a manner described hereinbefore in Example 1 to 3 for use in treating or preventing atherosclerosis.

EXAMPLE 7

Fenofibrate tablets containing 250 mg fenofibrate are prepared employing conventional procedures containing the following additional ingredients: corn starch, ethyl cellulose, glycerin, hydroxypropyl cellulose, hydroxypropylmethyl cellulose 2910, iron oxide, lactose, magnesium stearate, microcrystalline cellulose, polysorbate 80, talc and titanium dioxide.

The fenofibrate tablets are employed with 5 mg lisinopril tablets for treating or preventing atherosclerosis.

EXAMPLE 8

Tablets of the following compositions are prepared as described below.

| Ingredient | Weight (mg) |
|---|---|
| (E,E)-[difluoro[hydroxy(4,8,12-trimethyl-3,7,11-tridecatrienyl)-phosphinyl]methyl]phosphonic acid tripotassium salt (squalene synthetase inhibitor prepared as described by Biller et al. supra) | 100 mg |
| Avicel | 112.5 mg |
| Lactose | 113 mg |
| Cornstarch | 17.5 mg |
| Stearic Acid | 7 mg |
| | 350 mg |

The tablets are prepared from sufficient bulk quantities by slugging the squalene synthetase inhibitor Avicel, and a portion of the stearic acid. The slugs are ground and passed through a #2 screen and then mixed with the lactose, cornstarch, and the remainder of stearic acid. The mixture is compressed into 350 mg capsule shaped tablets in a tablet press. The tablets are scored for dividing in half.

The squalene synthetase inhibitor tablets may be administered as in accordance with the teachings of the present invention together with 5 mg captopril tablets to treat or prevent arteriosclerosis.

EXAMPLES 9 and 10

Lovastatin tablets are prepared employing conventional pharmaceutical techniques containing 20 mg lovastatin, cellulose, color, lactose, magnesium stearate and starch and butylated hydroxyanisole as a preservative as described in the 1990 PDR.

The lovastatin tablets may be employed in combination with the fenofibrate tablets (described in Example 7) in separate or combined dosage forms to treat or prevent atherosclerosis in accordance with the present invention.

EXAMPLES 11 to 12

A formulation in the form of tablets having the following composition is prepared as described in Example 1.

| Ingredient | Weight (mg) |
|---|---|
| (E,E,E)-[difluoro[hydroxy(4,8,12-trimethyl-1,3,7,11-tridecatetraenyl)phosphinyl]methyl]-phosphonic acid tripotassium salt (squalene synthetase inhibitor prepared as described by Biller et al. supra) | 100 mg |
| Cornstarch | 50 mg |
| Gelatin | 7.5 mg |
| Avicel (microcrystalline cellulose) | 25 mg |
| Magnesium stearate | 2.5 mg |
| | 185 mg |

The above formulations with captopril tablets, or ceranapril tablets may be employed in separate dosage forms or combined in a single capsule form to treat atherosclerosis in accordance with the present invention.

EXAMPLE 13

Probucol tablets containing 250 mg probucol are prepared employing conventional procedures containing the following additional ingredients as set out in the 1990 PDR: corn starch, ethyl cellulose, glycerin, hydroxypropyl cellulose, hydroxypropylmethyl cellulose 2910, iron oxide, lactose, magnesium stearate, microcrystalline cellulose, polysorbate 80, talc and titanium dioxide.

The ACE inhibitor formulations described in the previous examples may be employed with probucol tablets as a combination in accordance with the teachings of the present invention to treat atherosclerosis. In addition, any or all of the above drugs and probucol tablets may be ground up into powders and used together in a single capsule.

EXAMPLE 14

Capsules containing 300 mg gemfibrozil are prepared employing conventional pharmaceutical techniques containing the following additional ingredients as described in the 1990 PDR: polysorbate 80 NF, starch NF and silica gel.

The gemfibrozil capsules may be administered as a combination with any of the ACE inhibitor tablets and may be ground into a powder and used in a single capsule containing gemfibrozil and ACE inhibitor to treat atherosclerosis.

EXAMPLES 15

ACE inhibitor tablets as described above may be employed in combination with cholestyramine resin containing 4 g cholestyramine, acacia, citric acid, color, flavor, polysorbate 80, propylene glycol alginate and sucrose as described in the 1990 PDR to treat atherosclerosis in accordance with the present invention.

EXAMPLES 16

ACE inhibitor tablets, described above may be employed in combination with nicotinic acid, colestipol, dextrothyroxine or other serum cholesterol lowering agent in accordance with the teaching of the present invention to treat or prevent atherosclerosis.

It will also be appreciated that any of the cholesterol lowering drugs may be employed in combination with any of the ACE inhibitors disclosed herein in accordance with the present invention.

EXAMPLE 17

The following experiment was carried out to show effect of a combination of an HMG CoA reductase inhibitor, namely, pravastatin, and an ACE inhibitor, namely captopril, on atherosclerosis.

Animals

Male $F_1$ hamsters were fed 0.3% cholesterol and 10% coconut oil.

Experimental Design

Four sets of hamsters were established (n=12–13 per group). The groups were controls, pravastatin (34 mg/kg/day), captopril (100 mg/kg/day) and pravastatin plus captopril (32 and 100 mg/kg/day, respectively). All animals were fed the same atherogenic diet. Pravastatin was delivered via the diet and captopril was gavaged daily. Hamsters in the control and pravastatin groups were gavaged with water. The animals were treated for 8 weeks. At 3 and 6 weeks the animals were fasted overnight and bled to determine plasma cholesterols and triglycerides. At 8 weeks, mean arterial pressure and heart rate were measured and then the animals were fixed by perfusing formalin. The aortic arch was stained with oil red O and the total area of the fatty streak (which consists of macrophage-foam cells) was measured by computer assisted image analysis.

Results

At 8 weeks the mean arterial pressure of the captopril and pravastatin plus captopril groups were 21% and 14%, respectively, lower than those of the controls. Heart rates of the same two groups were also 7% and 10%, respectively, less than those of control hamsters (Table 1). Pravastatin had no effect on blood pressure or heart rate.

TABLE 1

Body Weights, Mean Arterial Pressure and Heart Rate (mean ± SD) of Control and Treated Hamsters

| | Body Weight (g) | MAP mmHg | HR beats/min. | n |
|---|---|---|---|---|
| Control | 138 ± 11 | 139 ± 14 | 376 ± 20 | 10–13 |
| Pravastatin 34 mg/kg/day | 139 ± 8 | 138 ± 13 | 355 ± 27 | 12 |
| Captopril 100 mg/kg/day | 133 ± 12 | 110 ± 17$^a$ | 348 ± 22$^a$ | 12 |
| Pravastatin 33 mg/kg/day Captopril 100 mg/kg/day | 132 ± 30 | 120 ± 17$^a$ | 339 ± 24$^a$ | 11 |

MAP: Mean Arterial Pressure   HR: Heart Rate
$^a$P < 0.05 compared to control group (Tukey's Test).

The effects on plasma lipids are shown in Table 2.

At the level of the artery wall, pravastatin and captopril similarly reduced the area of the fatty streak by approximately 50% compared to the control group, and the two drugs together decreased lesion area by 73% (Table 3). Therefore the combination of pravastatin and captopril inhibited early atherosclerosis to a significantly greater degree than either drug alone.

TABLE 2

Plasma Lipids (mean ± SD) of Control and Treated Hamsters at 5 Weeks

| | TC mg/dl | VLDL + LDL-C mg/dl | HDL-C mg/dl | TG mg/dl | n |
|---|---|---|---|---|---|
| Control | 773 ± 134 | 694 ± 133 | 69 ± 5 | 1126 ± 470 | 12–13 |
| Pravastatin 34 mg/kg/day | 456 ± 107$^a$ | 339 ± 93$^a$ | 117 ± 7$^a$ | 185 ± 34$^a$ | 12 |
| Captopril 100 mg/kg/day | 660 ± 94 | 588 ± 83 | 72 ± 23 | 1105 ± 259 | 12 |

TABLE 2-continued

Plasma Lipids (mean ± SD) of Control and Treated Hamsters at 5 Weeks

| | TC mg/dl | VLDL + LDL-C mg/dl | HDL-C mg/dl | TG mg/dl | n |
|---|---|---|---|---|---|
| Pravastatin 33 mg/kg/day Captopril 100 mg/kg/day | 433 ± 50[a] | 320 ± 50[a] | 113 ± 10[a] | 179 ± 30[a] | 13 |

[a]$P < 0.05$ compared to control group (Tukey's Test).

TABLE 3

Effects on Fatty Streak Area in the Aortic Arch (mean ± SD) of Control and Treated Hamsters

| | Fatty Streak Area* $\mu m^2 \times 10^3$ | n |
|---|---|---|
| Control | 487 ± 231 | 6–13 |
| Pravastatin 34 mg/kg/day | 248 ± 119[b] | 6–12 |
| Captopril 100 mg/kg/day | 245 ± 154[c] | 6–12 |
| Pravastatin 33 mg/kg/day Captopril 100 mg/kg/day | 133 ± 79[a] | 6–13 |

*6 aortic arches per group were analyzed for fatty streak area
[a]$P < 0.050$ compared to control group (Tukey's Test).
[b]$P < 0.069$ compared to control group (Tukey's Test).
[c]$P < 0.064$ compared to control group (Tukey's Test).

What is claimed is:

1. A method for stabilizing or causing regression of atherosclerosis in a mammalian species, which comprises administering synergistic effective amounts to a mammalian species in need of such treatment an effective amount of a combination of a cholesterol lowering drug and an angiotensin converting enzyme inhibitor wherein a cholesterol lowering drug is pravastatin and an angiotensin converting enzyme inhibitor is ramipril.

2. The method as defined in claim 1, wherein atherosclerotic lesions are stabilized or made to regress.

3. The method as defined in claim 1, wherein the angiotension converting enzyme inhibitor is administered in single or divided doses of from about 0.1 to about 500 mg/one to four times daily.

4. The method as defined in claim 1, wherein the angiotension converting enzyme inhibitor is administered to a normotensive patient.

5. The method as defined in claim 1, wherein the cholesterol lowering drug is present in a weight ratio to said angiotensive converting enzyme inhibitor of within the range of from about 0.001:1 to about 1000:1.

6. The method as defined in claim 1, wherein said angiotensin converting enzyme inhibitor is administered in single or divided doses of from about 0.1 to about 500 mg one to four times daily.

7. A pharmaceutical combination comprising synergistic effective amounts of an inhibitor of the enzyme 3-hydroxy-3-methyl-glutaryl coenzyme A (HMG CoA) reductase which is pravastatin and an ACE inhibitor which is ramipril.

8. The combination as defined in claim 7 wherein pravastatin is present in a weight ratio to the ACE inhibitor within the range of from about 0.001:1 to about 1000:1.

9. The method as defined in claim 1, wherein the cholesterol lowering drug is employed in a weight ratio to the angiotensin converting enzyme inhibitor within the range from about 0.05:1 to about 100:1.

* * * * *